United States Patent
Valla

(10) Patent No.: US 8,192,453 B2
(45) Date of Patent: Jun. 5, 2012

(54) SURGICAL CUTTING TOOL AND SYSTEM

(76) Inventor: Joseph R. Valla, Oak Creek, WI (US)

( * ) Notice: Subject to any disclaimer, the term of this patent is extended or adjusted under 35 U.S.C. 154(b) by 1130 days.

(21) Appl. No.: 11/724,980

(22) Filed: Mar. 16, 2007

(65) Prior Publication Data

US 2007/0233132 A1    Oct. 4, 2007

Related U.S. Application Data

(60) Provisional application No. 60/782,897, filed on Mar. 16, 2006.

(51) Int. Cl.
*A61B 17/16* (2006.01)
(52) U.S. Cl. .......................... 606/180; 606/80
(58) Field of Classification Search .................... 408/80, 408/202; 606/79–81, 86 R, 167, 170–171, 606/179–180; 623/22.21–22.29, 22.3, 22.31–22.39, 623/22.4, 22.41–22.46, 23.11–23.13
See application file for complete search history.

(56) References Cited

U.S. PATENT DOCUMENTS

| | | | | |
|---|---|---|---|---|
| 5,514,141 | A * | 5/1996 | Prizzi, Jr. ......................... | 606/80 |
| 7,763,031 | B2 * | 7/2010 | Tulkis ............................. | 606/99 |
| 2006/0015111 | A1 * | 1/2006 | Fenton ............................ | 606/80 |
| 2006/0079906 | A1 * | 4/2006 | Timperley et al. .............. | 606/81 |

* cited by examiner

Primary Examiner — Thomas C. Barrett
Assistant Examiner — Larry E Waggle, Jr.
(74) Attorney, Agent, or Firm — John Chiatalas

(57) ABSTRACT

A surgical cutting tool, instrument, kit and system are disclosed, which are adapted for use during in total hip (or shoulder) replacement surgery. The invention optimally and efficiently removes excess bone (osteophytes) and soft tissue from the rim of a hemispherical component such as an implanted acetabular shell, prior to insertion of a liner. The surgical instrument includes an elongated obturator adapted to be removably attached to the acetabular component. An elongated reamer tool has a cannulated central boss for receiving the obturator. The tool has an upper end adapted to be coupled to a powered tool driver, and a lower end provided with a pair of spaced apart blades adapted to engage the rim of the acetabular component and be driven to remove the excess bone fragments from the rim of the implanted shell component.

21 Claims, 6 Drawing Sheets

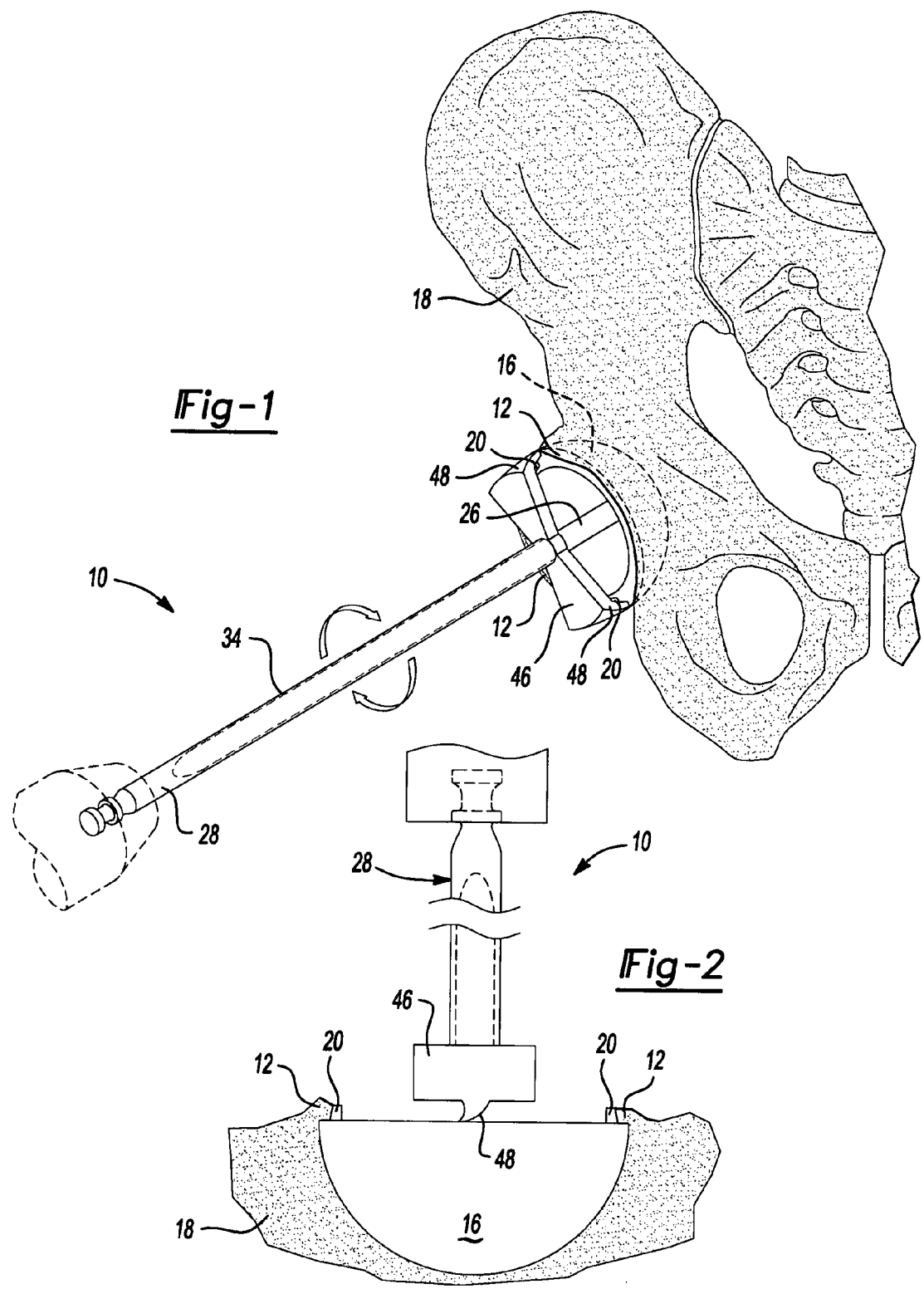

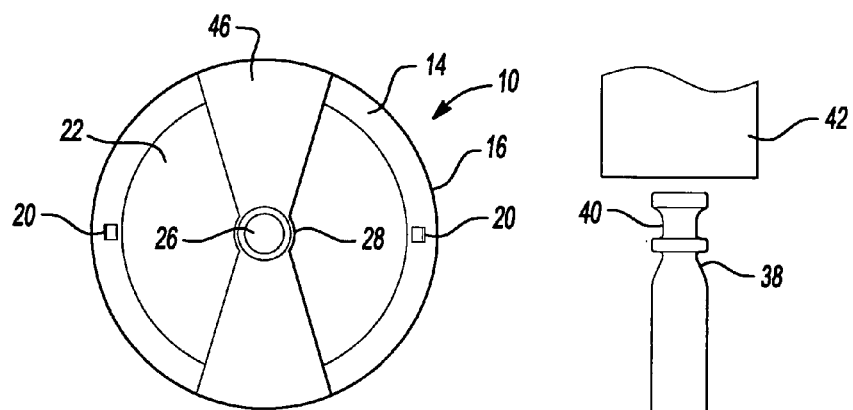
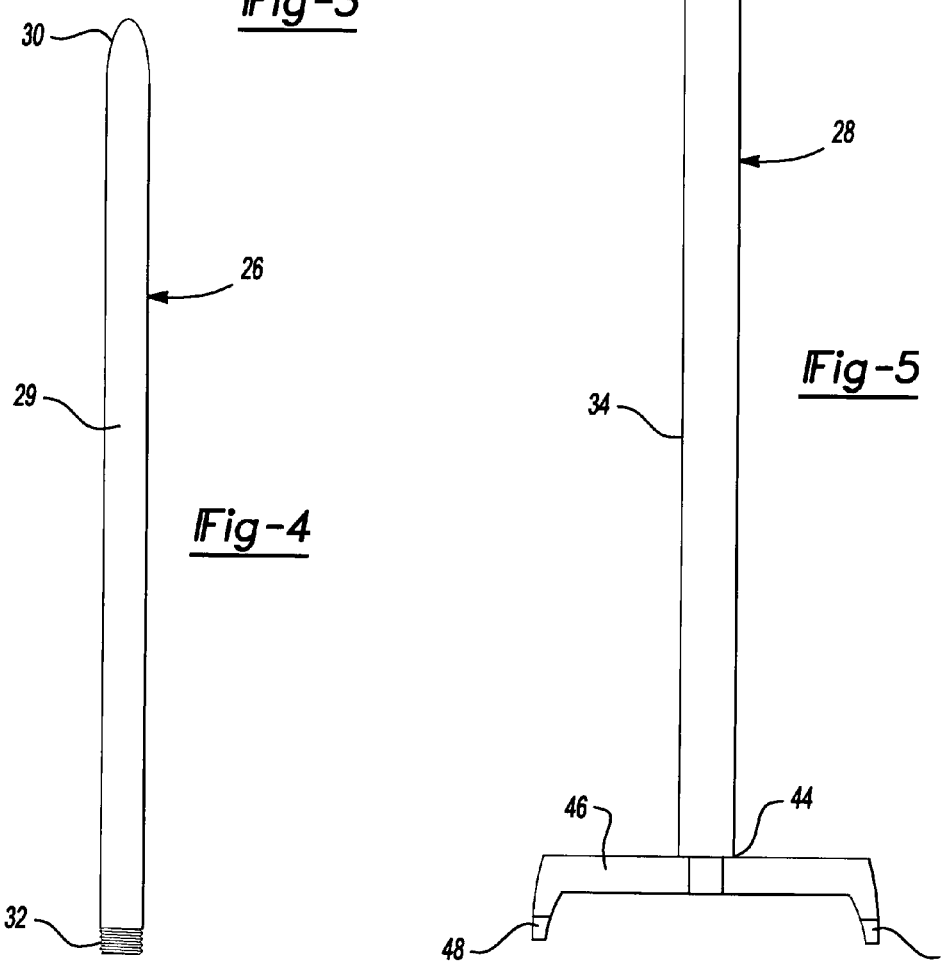

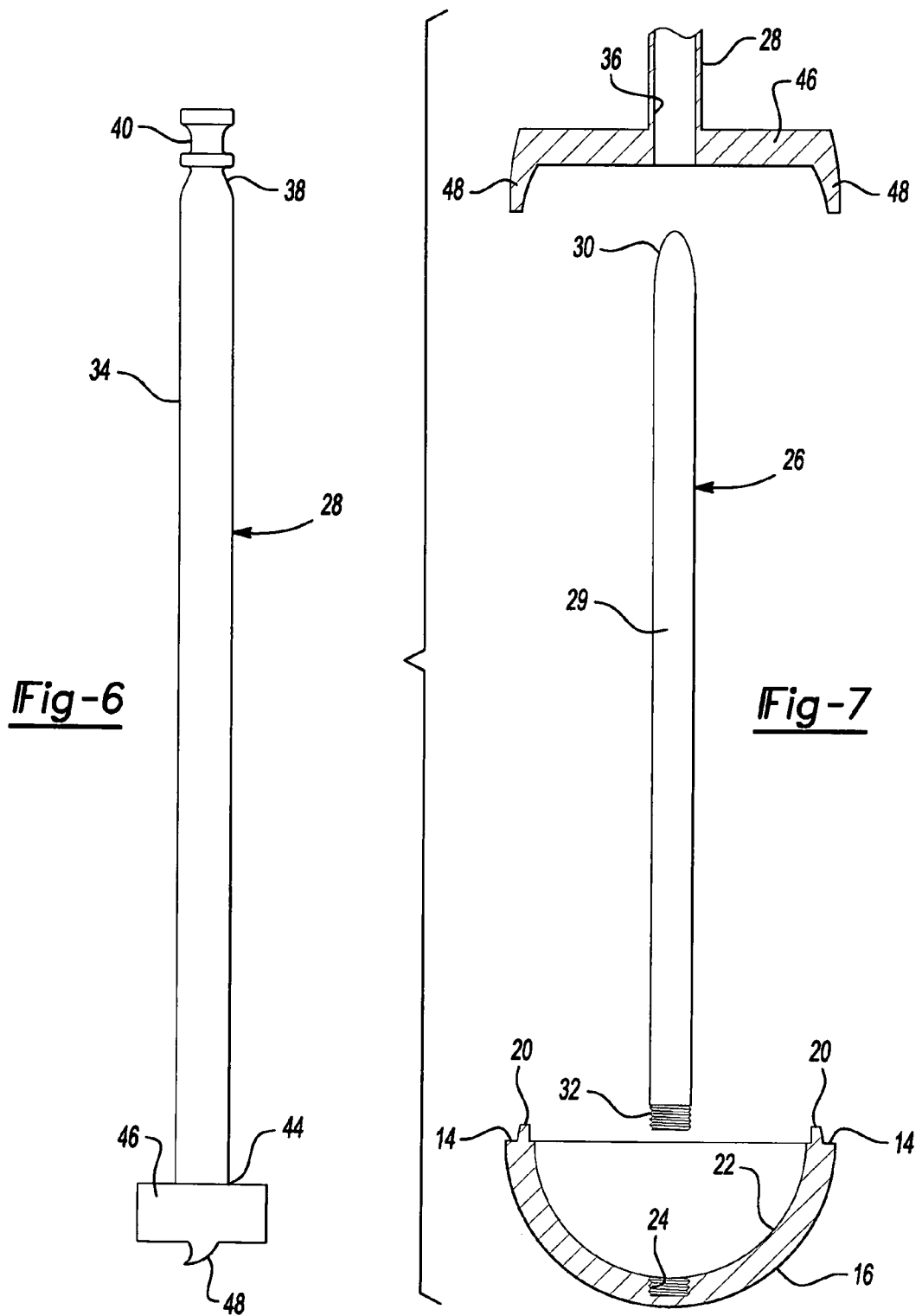

SURGICAL CUTTING TOOL AND SYSTEM

RELATED APPLICATIONS

This application claims priority from U.S. Provisional Utility Application No. 60/782,897, filed Mar. 16, 2006 by the present inventor, the entire contents of which are expressly incorporated by reference herein and relied-upon.

TECHNICAL FIELD

The present invention generally relates to surgical cutting tools and instrumentation systems that utilize such tools, as well as surgical kits incorporating arrays of these tools and instruments. The invention relates particularly to total joint arthroplasty where a hemispherical bone cavity such as a glenoid or acetabular cavity and more particularly, an acetabulum, is prepared to receive an implantable prosthetic component.

BACKGROUND

In orthopedic surgery, total joint replacement (also called joint arthroplasty) is performed where indicated on patients suffering from diseased bone due to osteoarthritis. Prosthetic components replace the end of the bone and the corresponding socket of the articulating bone that together form, e.g., a hip or shoulder joint. In the more common case of hip arthroplasty, the femur, the ball of the hip (head of the femur) and the cup of the hip (acetabulum) are replaced by endoprosthetic implants. Hip implants typically comprise two main components. The femoral component is anchored within the existing femur and includes a head that replaces the natural head of the femur. The acetabular component is secured within the acetabulum of the patient and serves as a bearing surface for the femoral component.

Most acetabular components include an outer shell or cup module and an internal liner, both of which have a semi-hemispherical shape. The outer shell has an outer dimension configured to fit and be fixed within the acetabulum of the patient. The outer shell is typically formed from a high strength metal such as stainless steel or titanium, in order to withstand the biomechanical forces exerted on the hip joint during normal activities. The inner liner is designed to be seated inside the outer shell by a locking ring or other retainer structure so that the liner locks within the shell. The inner liner is typically constructed of a polymeric material such a polyethylene. The liner serves much the same function as cartilage does in a healthy hip—it prevents the metal parts of the prosthetic joint from rubbing against each other.

The acetabulum is reamed and the proper outer shell size is determined by the surgeon. An example of a reaming system is disclosed in U.S. Pat. No. 5,658,290, including a surgical driver connecting with a domed cutting tool via catches that receive a pair of orthogonal bars from the tool. The tool presents an array of cutting teeth to form the hemispherical bone cavity of the acetabulum when rotated by the driver. The outer shell is positioned, aligned and then press fit into the reamed cavity, typically with the aid of an impact tool. The outer shell can be secured such as by screws which are inserted through a cluster of screw holes provided in the lower portion of the shell. Screw placement generally occurs in the posterior superior and/or posterior inferior quadrants of the acetabulum. The shell may be otherwise retained in the acetabulum, as will be appreciated by those skilled in the art.

At this point, the inner liner needs to be inserted into the outer shell. Before the liner is installed, there can be abnormal projections of bone (also known as "osteophytes") usually caused by increased stress or wear on the ends of bones, as well as soft tissue, which protrude over the peripheral rim of the outer shell and interfere with the immediate placement of the liner. Traditionally, these protrusions have been cleared away by use of an osteotome (a chisel-like instrument) and a rongeur in a manner which is not optimally efficient. When the osteophytes and soft tissue have finally been cleared from the outer shell periphery, liner placement may proceed using the locking ring inside the outer shell. The hip replacement procedure is then finished by securing the femoral component as is well known.

It is desirable to provide a surgical tool, instrument and kit allowing timelier, more efficient removal of excess bone and soft tissue from the periphery of the implanted outer shell, which improves placement of the inner liner during total hip replacement.

It is further desirable to provide surgical tools, instruments and kits, which function with existing prosthetic components and implantation systems.

Accordingly, there is a need to provide an improved means for osteophyte removal that further functions with existing rotary power drivers to track the shape of implantable components in the body of a patient without the risk of over-cutting. Particularly, there is a need for visual confirmation by the surgeon of the position of the tool as the osteophytes and excess soft tissue are being fully sheared.

There is a further need for a rotary cutting tool having a tooth design that precisely shears osteophytes and soft tissue along the desired periphery of an implantable cup received in the bone cavity, while employing a linear cut guided by accurate visual confirmation by the surgeon.

SUMMARY OF INVENTION AND ADVANTAGES

According to one aspect of the present invention, there is provided a surgical cutting tool adapted for clearing a periphery of a patient's glenoid or acetabular bone cavity. The tool includes a support member rotatable about an axis and presenting at least one cutting site spaced from the axis, wherein the tool describes a circular cutting profile generally superposable on the periphery of the cavity as the support member is rotated about its axis in a predetermined spatial relationship with the cavity to shear osteophytes and excess soft tissue at the cutting site.

In a preferred embodiment, the tool is adapted for clearing the periphery of the bone cavity along a rim of an acetabular shell component situated within the cavity in preparation for receiving an inner liner, the support member encompassing a dimension corresponding to a diameter of the shell. In another preferred embodiment, the tool includes a plurality of the cutting sites having teeth juxtaposed with the rim, respectively. In yet another preferred embodiment, the support member has an elongate shape with a centering boss and arms extending radially from the boss, the arms having ends with teeth depending downwardly toward the rim. In still another preferred embodiment, there is provided a mechanism for positioning the support member wherein the cutting profile is maintained in proper juxtaposed relationship with the rim. In a further preferred embodiment, there is provided a locking mechanism on the support member wherein the cutting profile is maintained in proper juxtaposed relationship with the rim. In yet a further preferred embodiment, the cutting sites are on modular cutting sections corresponding in size with different shells. In still a further preferred embodiment, the cutting sites have teeth depending downwardly toward the rim and curved away from the rotational direction of the cutting profile, respectively. In another further preferred embodiment, there is a graduated adjustment mechanism for maintaining the cutting profile in a selected spatial relationship with the rim.

According to a second aspect of the present invention, a surgical instrument is provided for clearing a periphery of a patient's glenoid or acetabular bone cavity surrounding a prosthetic component. The instrument includes a cutting tool having a support member rotatable about an axis and presenting at least one cutting site spaced from the axis. The instrument also includes a centering member articulating with the support member along the axis. The tool describes a circular cutting profile generally superposable on the rim as the support member is rotated about the centering member in a predetermined spatial relationship with the cavity to shear osteophytes and excess soft tissue at the cutting site.

In a preferred embodiment, the instrument is adapted for clearing the rim of an acetabular shell component situated within the cavity in preparation for receiving an inner liner, the support member encompassing a dimension corresponding to a diameter of the shell. In another preferred embodiment, a plurality of cutting sites has teeth juxtaposed with the rim, respectively. In yet another preferred embodiment, the support member has an elongate shape with a centering boss and arms extending radially from the boss, the arms having ends with teeth depending downwardly toward the rim. In still another preferred embodiment, the support member further includes a boss and the centering member is an obturator received by the boss for aligning the cutting profile in juxtaposition with the rim as the tool is rotated about the axis. In a further preferred embodiment, a locking mechanism releasably connects the support member to the centering member. In yet a further preferred embodiment, the cutting sites are modular cutting sections corresponding in size with different shells. In still a preferred embodiment, the cutting sites have teeth depending downwardly toward the rim and curved away from the rotational direction of the cutting profile, respectively. In another further preferred embodiment, there is a graduated adjustment mechanism for maintaining the cutting profile in a selected spatial relationship with the rim.

In a preferred aspect of the invention, there is provided a surgical instrument adapted to be used during total hip replacement in removing excess bone and soft tissue from the rim of an acetabular component implanted in a patient's acetabulum prior to insertion of a liner. The surgical instrument includes an elongated obturator adapted to be removably attached to the acetabular component. An elongated reamer tool has a cannula for receiving the obturator. The tool has an upper end adapted to be coupled to a powered tool driver, and a lower end provided with a pair of spaced apart blades adapted to engage the rim of the acetabular component and be driven to remove the excess bone fragments from the rim of the implanted acetabular component.

According to a third aspect of the present invention, there is disclosed a joint arthroplasty surgical kit. The kit has an array of rimmed hemispherical implant components and instrumentation for clearing the periphery of an acetabular or glenoid bone cavity to receive the components. The kit instrumentation includes an array of cutting tools each with a support member rotatable about an axis and presenting cutting sites spaced from the axis. The kit also includes an array of centering members adapted for removable attachment to the implant components and further articulating with the support members along the axis thereof. The tool describes a circular cutting profile generally superposable on the component rim as the tool is rotated about the centering member in a predetermined spatial relationship with the cavity to shear osteophytes and excess soft tissue at the cutting sites.

In a preferred embodiment, the kit further incorporates an array of trial prosthetic components of various sizes which are removable interoperatively, particularly in cases of revision surgeries. Various other preferred embodiments are contemplated vis-à-vis particular structural elements recited in the first and second aspects of the invention which are summarized above.

According to a fourth aspect of the present invention, there is contemplated a system for shoulder or hip joint arthroplasty to remove excess bone and soft tissue from the rim of a hemispherical component implanted in a patient's bone cavity prior to insertion of a liner in the component. The system includes provision for an elongated obturator having a lower end and an upper end, as for an elongated reamer tool having a cannula for receiving the obturator. The tool has an upper end adapted to be coupled to a powered tool driver, and a lower end having a pair of spaced apart bladed teeth. The lower end of the obturator is removably attached to the component with the cannula slid over the upper end of the obturator. The bladed teeth engage the rim of the component with the upper end of the tool coupled to the powered driver, rotating the tool relative to the obturator. This causes the bladed teeth to shear off the excess bone and soft tissue at the rim of the implanted component.

In a preferred embodiment, the system is particularly adapted for hip joint arthroplasty wherein the implanted hemispherical component is an acetabular shell.

An advantage of the present invention is the capability to make an accurate peripheral cut along the rim of an implantable hemispherical shell component, where the rim can be cleared of osteophytes and excess bone tissue in preparation for a liner component to be installed.

Another advantage of the invention is a tool presenting cutting sites that allow a full cut with clear visual confirmation while the tool is linearly stationary in the bone cavity, without needing to change the orientation of the surgical driver.

A further advantage of the invention is that, in preferred embodiments, the teeth are contained at peripheral cutting sites, which avoids risk of tissue entrapment.

Various other objects, features and advantages of the invention will be made apparent from the following Description taken together with the Drawings.

BRIEF DESCRIPTION OF THE DRAWINGS

The Drawings illustrate the best mode presently contemplated of carrying out the invention. In the Drawings:

FIG. 1 is an assembled view of a surgical instrument used to clean excess bone fragments away from the peripheral rim of an implanted acetabular component, showing a preferred curved tooth shape;

FIG. 2 is a view of FIG. 1 showing the surgical instrument rotated 90 degrees relative to the acetabular component;

FIG. 3 is a top view of FIG. 2;

FIG. 4 is an elevational view of an obturator forming one part of the surgical instrument;

FIG. 5 is an elevational view of a cannulated reamer tool forming another part of the surgical instrument;

FIG. 6 is a view like FIG. 5 rotated 90 degrees along a longitudinal axis of the reamer tool;

FIG. 7 is an exploded view of the reamer tool, the obturator and the acetabular component;

DETAILED DESCRIPTION

Figure 8:
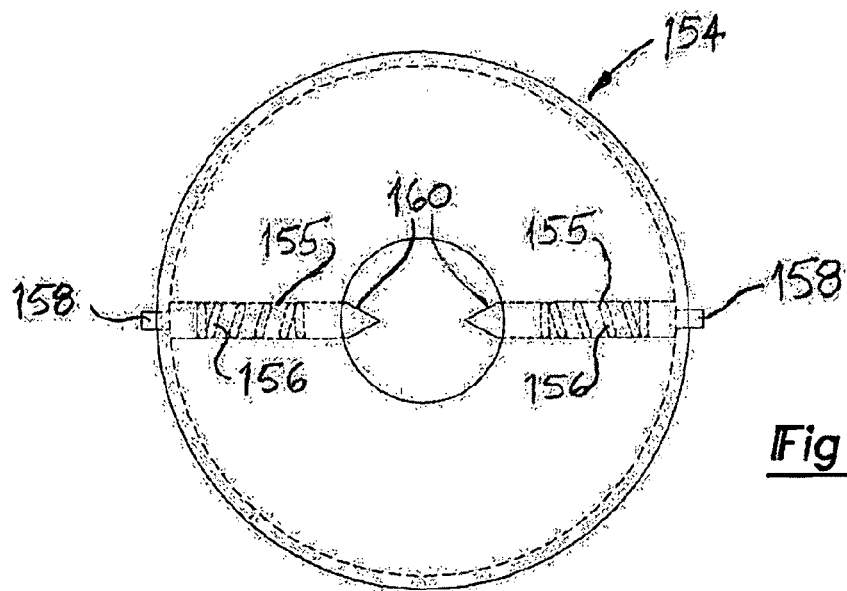
FIG. 8 is a top view of another surgical instrument used to clean excess bone fragments away from the peripheral rim of an implanted acetabular component.

Referring to FIGS. 1-3 of the Drawings, there is generally shown an assembled version of a surgical instrument 10 embodying the present invention. Surgical instrument 10 is particularly useful during a total hip replacement procedure in cleaning excess bone and soft tissue 12 which sometimes protrude from the peripheral rim 14 of a metallic acetabular component 16 (also known as a cup or outer shell) after the component or the shell 16 has been inserted and secured within a reamed cavity in a patient's pelvic acetabulum 18. As seen most clearly in FIG. 2, the osteophytes and soft tissue 12 lie outside the outermost faces of a pair of diametrically opposed tabs 20 or other suitable positioning members projecting upwardly from the rim of the shell 16. As is well know, the tabs 20 are used to position a polymeric liner (not shown) which acts as a bearing surface for a femoral head. The liner is intended to be inserted within the concave inner surface 22 (FIG. 3) of the shell 16. The inner surface 22 is normally smooth except for a central threaded recess 24 formed therein and a peripheral liner groove (not shown) for a locking ring.

The surgical instrument 10 is comprised of an elongated obturator 26 and an elongated cannulated reamer tool 28. The obturator 26 is a metal shaft 29 having an upper end 30 which may be tapered, and an opposite lower end 32 which is threaded to be removably engaged within the threaded recess 24 formed in the shell 16. The reamer 28 includes a cannula 34 forming a channel 36 which is designed to telescopically receive the obturator 26 along most of its length. An upper end 38 of the reamer 28 is provided with a power adaptor 40 that is received within a suitable powered driver 42 shown in phantom lines in FIG. 5. An opposite lower end 44 of the reamer 28 includes a blade holder 46 having a pair of spaced apart blades 48 which are designed to be positioned on the rim 14 of the shell 16 outside the tabs 20.

The surgical instrument 10 is used once the shell 16 has been properly implanted in the acetabulum 18, and the excess bone and soft tissue 12 must be cleared from the rim 14 of the shell 16 to enable proper locking of the liner. This is accomplished by first screwing the threaded lower end 32 of the obturator 26 so that the obturator shaft 29 is slidably received in the cannula 36 of the reamer 28. At the same time, the blades 48 on the reamer 28 rest upon the peripheral rim 14 of the shell 16 and the cutting surfaces of the blades 48 lie adjacent the outer surfaces of tabs 20. Now, the power tool driver 42 is coupled to the adaptor 40 on the upper end 38 of reamer 28, and the reamer 28 is rotated relative to the obturator 26. This causes the blades 48 rotating on the rim 14 of the shell 16 to shear off and clear away the osteophytes and soft tissue 12 in a timely and efficient manner which improves over the prior art impacting process. The result is a quick and uniform removal of bone and soft tissue from the periphery of the shell 16 so that liner installation and the rest of hip replacement may proceed once the reamer 28 is extracted from the oburator 26, and the obturator 26 is unscrewed from the shell 16.

Figure 9:
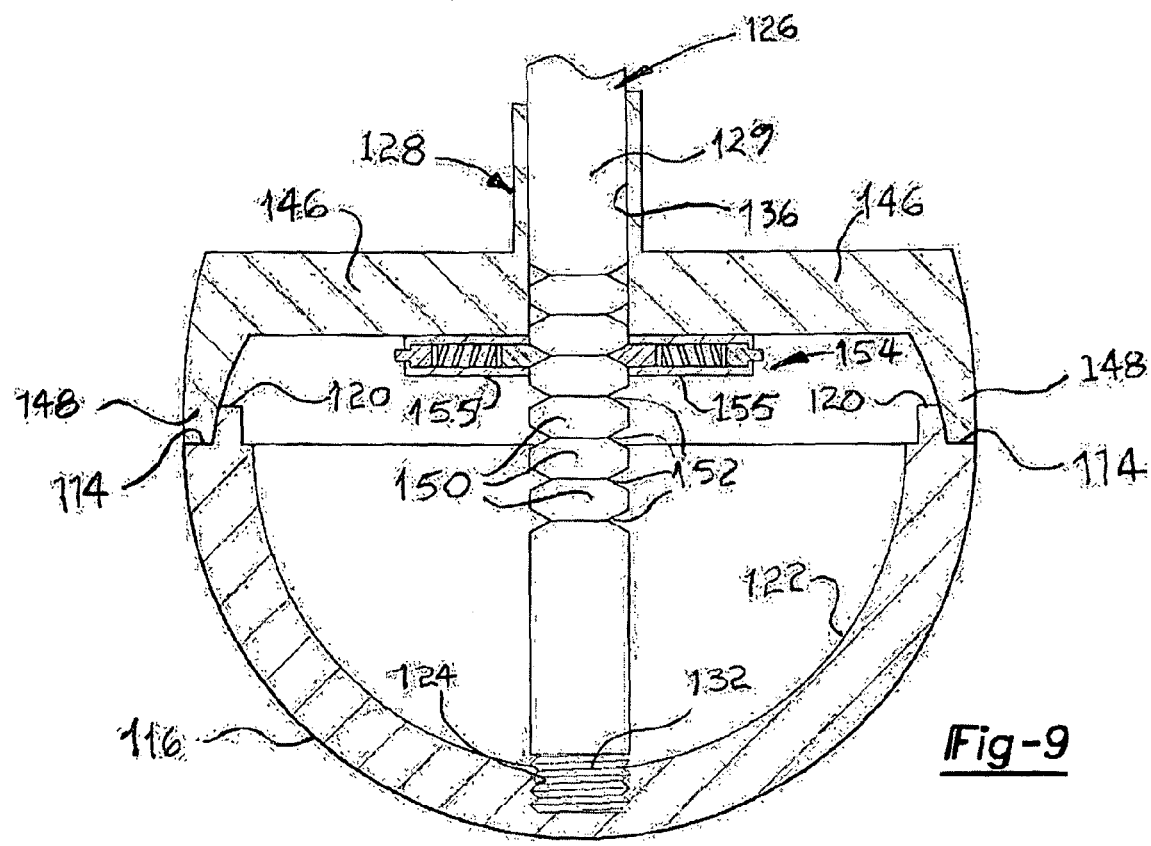
FIG. 9 is an exploded partial view of the reamer tool, the obturator and the acetabular component, showing preferred positioning and locking mechanisms for maintaining the instrument in alignment with its cutting profile juxtaposed with the component rim.
Figure 10:
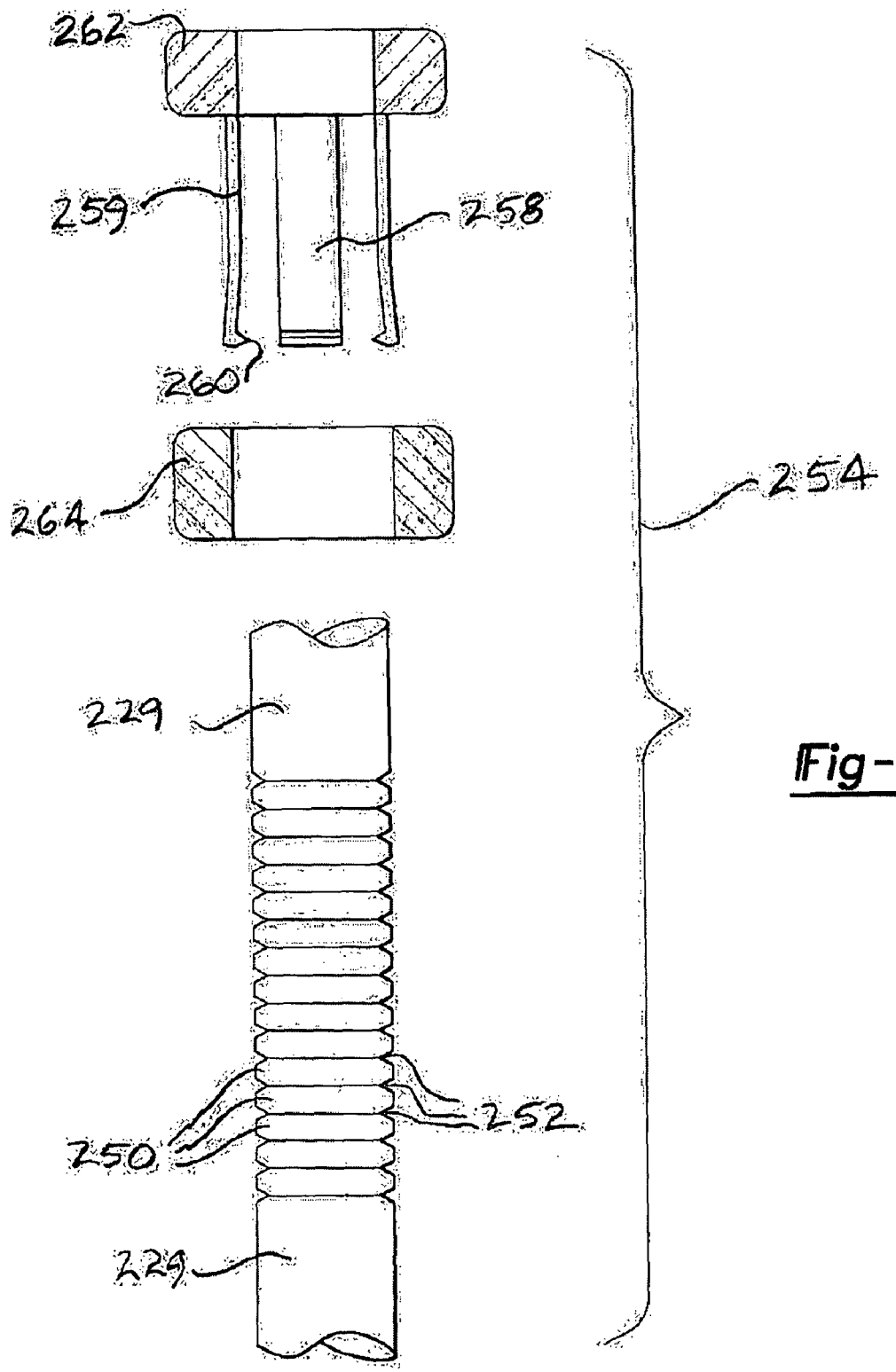
FIG. 10 is an exploded view of a preferred locking mechanism.
Figure 11A:
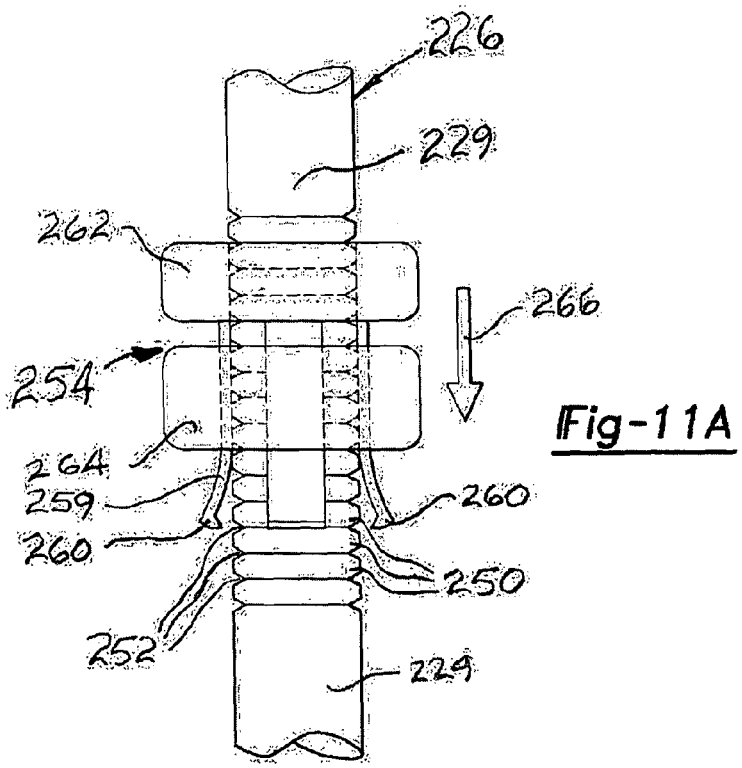
FIG. 11A is an elevational view of the locking mechanism showing its jaws received within the locking nut.
Figure 11B:
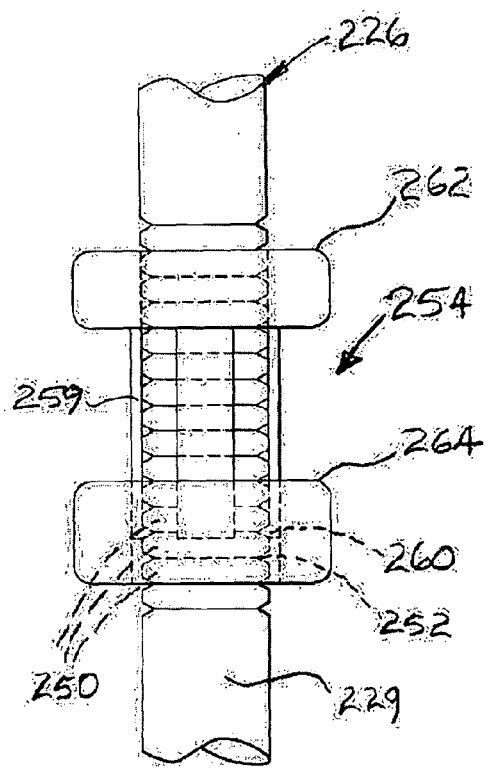
FIG. 11B a sequential view of FIG. 11A.

Referring to FIGS. 8-9, a positioning mechanism is generally shown at 154. Likewise, another type of positioning mechanism is generally shown at 254 in FIGS. 10 and 11A-11B. Analogous series of reference numerals in said Figures perform analogous functions to the counterparts described in FIGS. 1-7. Therefore, no attempt will be made to redundantly describe structural variants where similar functions are readily apparent to those skilled in the art who will appreciate the elucidating discussion already given. There is further shown one type of locking mechanism represented by one group of cooperating elements 150, 152, 155, 156, 160 (FIGS. 8-9) and another slightly different type of locking mechanism vis-à-vis a group of elements 250, 252, 259, 260, 262, 264 (FIGS. 10, 11A-11B), respectively. In FIGS. 8-9 the positioning mechanism 154 relies springs 155 biasing pointed pins 160 engaged by manual buttons 158, which are received between segments 150 in the V-shaped circular grooves 152 of obturator 126. Threads 132 of the obturator 126 engage threads 124 in cup surface 122, and the obturator, in turn, passes through cannulated boss 136 of tool 128. The support member 146 of reamer tool 128 with bearing bladed teeth 148 otherwise engage tabs 120 along rim 114 of cup 116 substantially as set forth in FIGS. 1-7. In FIGS. 10 and 11A-11B, the positioning mechanism 254 relies upon upper nut 262 with post 258 and tangs 259 being moved axially in the direction of arrow 266 in mating engagement with lower nut 264, which tightens the tangs 259 against obturator 126 so that barbs 260 lodge between segments 250 in grooves 252.

While one or more preferred embodiments of the present invention have been described, it should be understood that various changes, adaptations and modifications might be made without departing from the spirit of the invention and the scope of the appended Claims.

The invention claimed is:

1. A surgical debridement instrument for hip or shoulder joint arthroplasty comprising:

a support member with a boss rotatable by a powered driver about a longitudinal axis and support arms extending radially from the boss, the arms having downwardly depending teeth extending away from the driver and oriented parallel to the axis, respectively, generating a circular cutting profile as the tool is rotated about the axis;

an elongated obturator having opposed proximal and distal ends, an upper end engaging the boss to center the cutting profile and a lower end having a first connecting element for mating with an impactor connecting element formed within the apex of an implanted acetabular or glenoid cup component that defines a rim, axially spacing the support member from the distal end whilst aligning the obturator with the axis; and wherein the teeth have inboard faces that tangentially superpose over an outer diameter of the cup rim as the tool is rotated to generate the cutting profile, shearing osteophytes and excess soft tissue surrounding the rim without marring the outer diameter of the cup rim.

2. The instrument of claim 1 further comprising a cannula formed within the boss for telescopically receiving the upper end of the obturator to axially and radially position the support arms over the cup.

3. The instrument of claim 2 wherein the cannula further comprises a blind passage in which the upper end of the obturator bottoms-out a predetermined distance from the lower end of the obturator to axially position the support arms relative to the cup rim.

4. The instrument of claim 1 further comprising a positioning mechanism that releasably couples the obturator and support member together.

5. The instrument of claim 4 further comprising a series of grooves formed in the obturator at discrete intervals and wherein the boss has a lock with a spring-loaded catch that selectively engages the grooves to longitudinally arrest the support member relative to the obturator.

6. The instrument of claim 1 wherein the teeth are affixed on modular sections of the support member that are movable transverse to the boss, radially adjusting the teeth to different outer cup diameter sizes.

7. The instrument of claim 1 wherein the teeth further comprise blades that are curved away from the rotational direction of the cutting profile, respectively.

8. The instrument of claim 1 wherein a pair of the support arms extend diametrically in opposed radial directions from the boss and perpendicular to the longitudinal axis of the obturator.

9. An orthopedic surgical instrumentation kit comprising:
(a) an array of differently sized reamer tools rotatable by a driver, each tool forming a T-shape defining a shaft extending between opposed upper and lower ends along a longitudinal axis and a pair of support arms extending in diametrically opposed directions from a boss defining an I-shape with the boss centered between opposed terminal ends of the arms, each arm presenting a downwardly depending bladed tooth with an inner face and a cutting edge, respectively, each arm delimiting a selected dimension for each tool in the array, with corresponding cutting edges being rotatable about the axis to generate a circular cutting profile;
(b) at least one obturator extending between a lower end with a first connecting element and an upper end that telescopically engages the boss, centering the tool along the axis; and
(c) an array of differently sized implantable acetabular or glenoid cup components each defining a hollow hemispherical shape having an internal apex presenting a second connecting element formed therein that mates with the first connecting element, each cup including a rim having an outer diameter that matches the circular cutting profile, wherein the shaft is rotated about the drive axis shearing osteophytes and excess soft tissue surrounding the rim.

10. The kit of claim 9 further comprising a cannula formed in the shaft into which the boss opens to telescopically receive a discrete length of the upper obturator end, superposing the support arms over the cup.

11. The kit of claim 9 further comprising a positioning mechanism that couples the obturator and a support member of the reamer tool together for a pre-determined length.

12. The kit of claim 11 further comprising a lock with a spring-loaded catch that engages any of a series of grooves formed in the obturator at discrete intervals.

13. The kit of claim 11 wherein the positioning mechanism along with the support member define a plurality of differently sized obturators.

14. The kit of claim 9 wherein the blades form part of modular sections, respectively, allowing adjustment of the selected dimension to different outer cup diameter sizes.

15. The kit of claim 9 wherein the blades are curved away from the rotational direction of the cutting profile, respectively.

16. An orthopedic surgical system that comprises:
(a) providing a debridement tool forming a T-shape defining
(i) a shaft extending between an upper end and a lower end, along an axis rotatable by a power driver,
(ii) a support member having diametrically opposed arms with a boss centered between opposed terminal ends of the arms,
(iii) bladed teeth depending downwardly away from the driver and presented on the terminal ends, respectively, each blade spaced a selected distance from the boss with an inner face and a cutting edge, the tool being rotatable by the driver about the axis to generate a circular cutting profile;
(b) providing an elongated obturator extending between a lower end presenting a first connecting element and an upper end telescopically engageable with the boss;
(c) providing an implantable acetabular or glenoid cup component defining a hollow hemispherical shape with
(i) a rim having an outer diameter matching the distance between opposed teeth on the respective arms and
(ii) an internal apex presenting a second connecting element; and
(d) aligning the obturator along the axis, fastening the first and second connecting elements together, rotatably engaging the upper end of the obturator with the boss and suspending the terminal ends over the rim with the inner surface of the teeth tangentially engaging the outer diameter of the rim, rotating the shaft about the axis generating the circular cutting profile, and shearing osteophytes and excess soft tissue surrounding the rim.

17. The system of claim 16 wherein the boss of (a)(ii) opens into a tubular portion of the shaft of (a)(i) that telescopically receives a pre-determined length of the obturator sufficient to suspend the tool above the cup rim of (c)(i) while engaging the cutting edges of (a)(iii) with the outer diameter of the rim.

18. The system of claim 16 wherein a positioning mechanism couples the obturator and support member together for the pre-determined length.

19. The system of claim 18 further comprising a lock including a spring-loaded catch that adjustably engages any of a series of grooves formed in the obturator at discrete intervals.

20. The system of claim 16 wherein the support member defines an I-shape with a pair of opposed arms extending radially from the boss perpendicular to the drive axis.

21. The system of claim 16 wherein the blades are curved away from the rotational direction of the cutting profile, respectively.

* * * * *